United States Patent
Nicewicz et al.

(10) Patent No.: US 9,365,530 B2
(45) Date of Patent: Jun. 14, 2016

(54) DIRECT ANTI-MARKOVNIKOV ADDITION OF ACIDS TO ALKENES

(71) Applicant: The University of North Carolina at Chapel Hill, Chapel Hill, NC (US)

(72) Inventors: David A. Nicewicz, Durham, NC (US); David S. Hamilton, Carrboro, NC (US); Andrew J. Perkowski, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/397,603

(22) PCT Filed: May 6, 2013

(86) PCT No.: PCT/US2013/039707
§ 371 (c)(1),
(2) Date: Oct. 28, 2014

(87) PCT Pub. No.: WO2013/169651
PCT Pub. Date: Nov. 14, 2013

(65) Prior Publication Data
US 2015/0133680 A1    May 14, 2015

Related U.S. Application Data

(60) Provisional application No. 61/643,485, filed on May 7, 2012.

(51) Int. Cl.
| | |
|---|---|
| C07D 313/00 | (2006.01) |
| C07D 307/12 | (2006.01) |
| B01J 31/02 | (2006.01) |
| B01J 35/00 | (2006.01) |
| C07D 307/06 | (2006.01) |
| C07D 309/04 | (2006.01) |
| C07D 313/04 | (2006.01) |

(52) U.S. Cl.
CPC ........... *C07D 307/12* (2013.01); *B01J 31/0235* (2013.01); *B01J 31/0239* (2013.01); *B01J 31/0244* (2013.01); *B01J 35/004* (2013.01); *C07D 307/06* (2013.01); *C07D 309/04* (2013.01); *C07D 313/04* (2013.01); *B01J 2231/324* (2013.01); *B01J 2531/002* (2013.01); *B01J 2531/008* (2013.01)

(58) Field of Classification Search
CPC ...................................................... C07D 307/12
USPC ......................................................... 549/346
See application file for complete search history.

(56) References Cited

U.S. PATENT DOCUMENTS

| | | | |
|---|---|---|---|
| 7,282,617 | B2 | 10/2007 | Schinski et al. |
| 2008/0021071 | A1 | 1/2008 | Gravestock et al. |

FOREIGN PATENT DOCUMENTS

WO    WO 2005/077885 A1    8/2005

OTHER PUBLICATIONS

Bruneau et al. Accounts of Chemical Reaserch, 1999, 32, 311-323.*
Wilger et al., Nature Chemistry, 2014, 6, 720-726.*
Perkowski et al J. Am. Chem. Soc. 2013, 135, 10334-10337.*
International Search Report and Written Opinion, PCT/US2013/039707, mailed Aug. 29, 2013.
Beller M et al. Catalytic Markovnikov and anti-Markovnikov functionalization of alkenes and alkynes: recent developments and trends. Angew. Chem. In ed. 2004; 43(26): 3368-3398.
Bruneau C and Dixneuf PH. Metal vinylidenes in catalysis. Acc. Chem. Res. 1999; 32(4): 311-323.
Hamilton DS and Nicewicz DA. Direct catalytic anti-Markovnikov hydroetherification of alkenols. J. Am. Chem. Soc. Oct. 31, 2012; 134: 18577-18580.
Nguyen TM and Nicewicz DA. Anti-Markovnikov hydroamination of alkenes catalyzed by an organic photoredox system. J. Am. Chem. Soc. Jun. 14, 2013; 135: 9588-9591.
Perkowski AJ and Nicewicz DA. Direct catalytic anti-Markovnikov addition of carboxylic acids to alkenes. J. Am. Chem. Soc. Jul. 1, 2013; 135: 10334-10337.

* cited by examiner

*Primary Examiner* — Nizal Chandrakumar
(74) *Attorney, Agent, or Firm* — Myers Bigel & Sibley, P.A.

(57) ABSTRACT

A method of making an anti-Markovnikov addition product is carried out by reacting an acid with an alkene or alkyne in a dual catalyst reaction system to the exclusion of oxygen to produce said anti-Markovnikov addition product; the dual catalyst reaction system comprising a single electron oxidation catalyst in combination with a hydrogen atom donor catalyst. Compositions useful for carrying out such methods are also described.

5 Claims, 3 Drawing Sheets

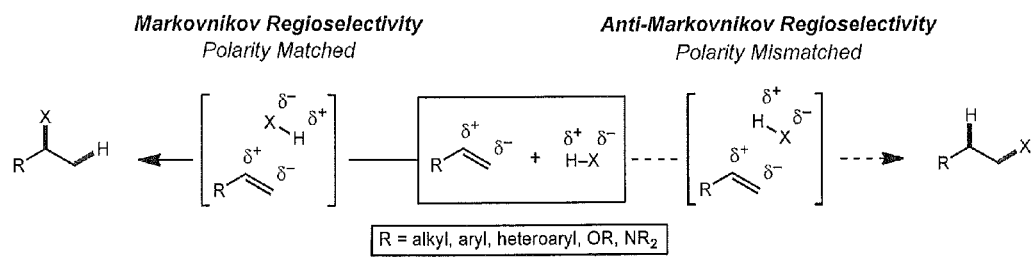
Fig. 1. Regioselectivity in addition reactions of mineral and organic acids to olefins.
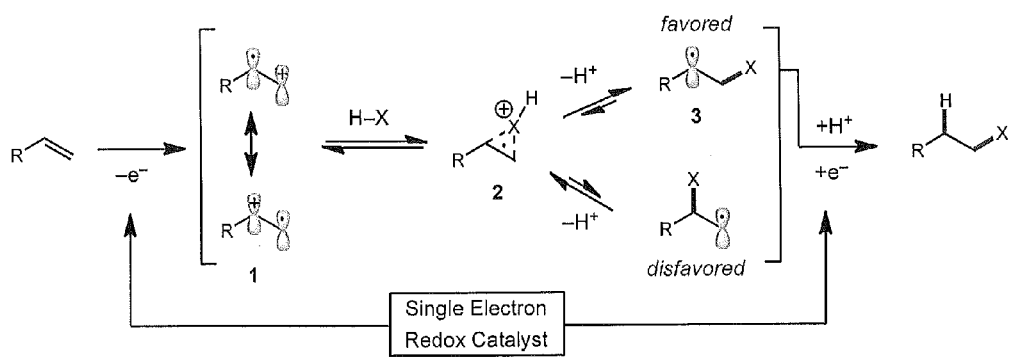
Fig. 2. Cation radicals as potential reactive intermediates in anti-Markovnikov addition reactions of acids to alkenes.

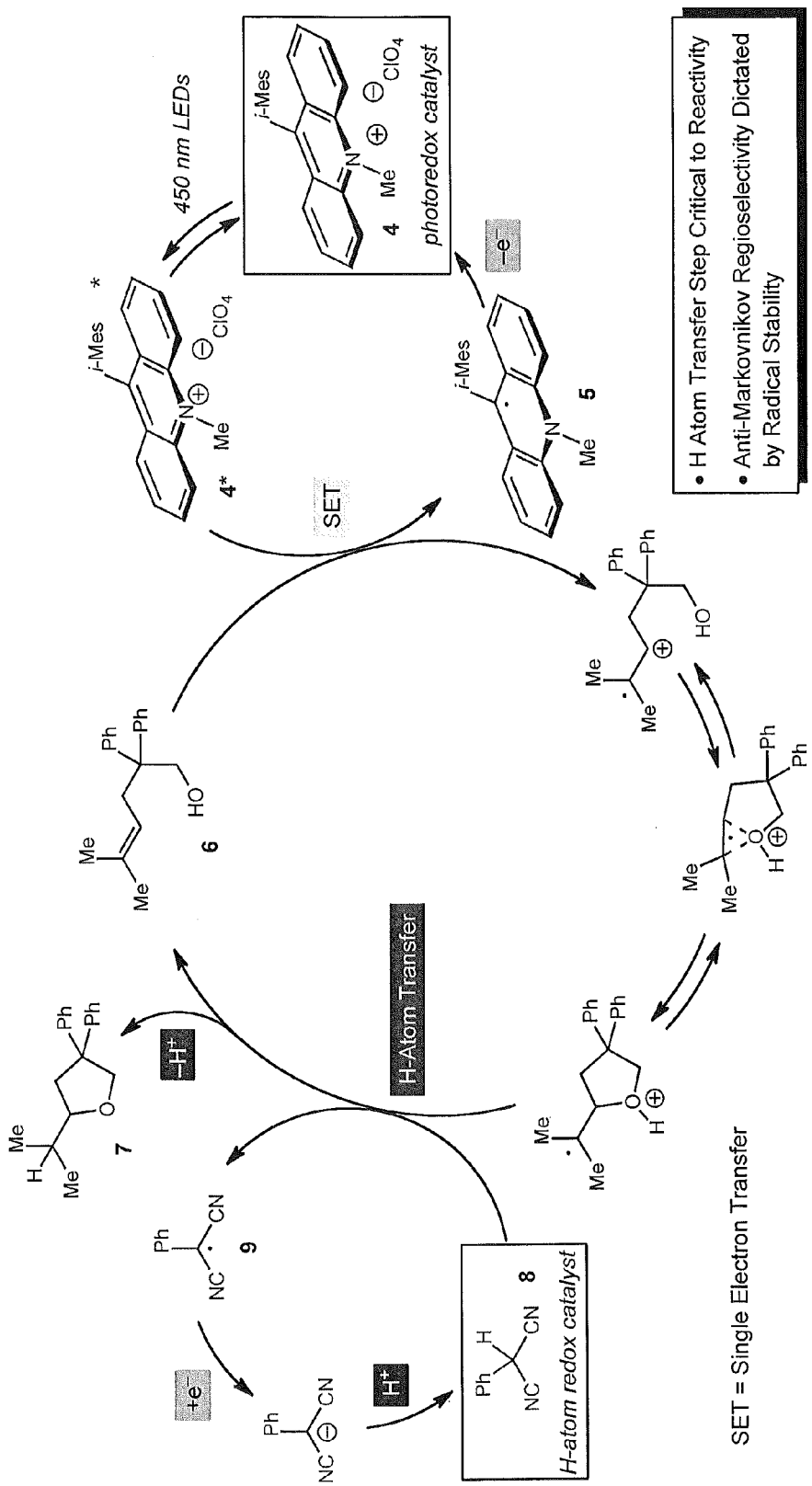
Fig. 3. Proposed Catalytic Cycle for Intramolecular Alkene Anti-Markovnikov Hydroalkoxylation.

*Intramolecular Anti-Markovnikov Hydrolactonization*
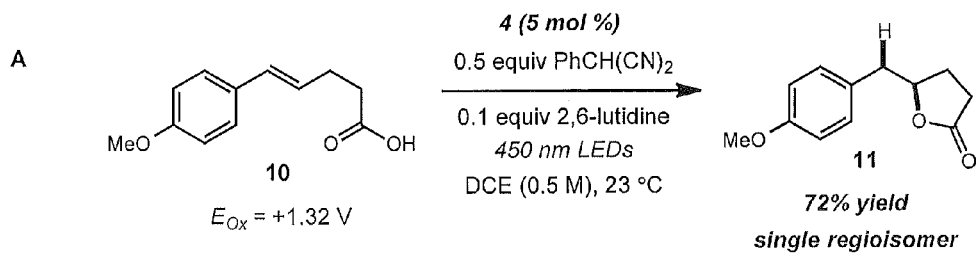
*Intermolecular Anti-Markovnikov Hydroacetoxylation*
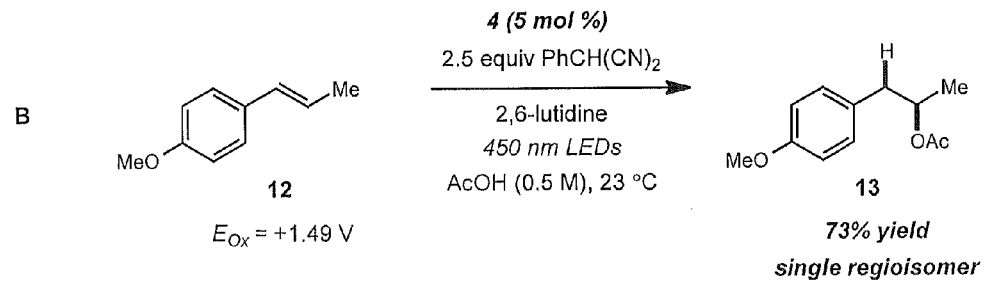
Fig. 4. (A) Alkene anti-Markovnikov hydrolactonization catalyzed by 4. (B) Anti-Markkovnikov addition of acetic acid to anethole catalyzed by 4. Alkene oxidation potentials were measured in MeCN with 0.1 M Bu4N+ClO4− and Ag/AgCl as the reference electrode.

US 9,365,530 B2

DIRECT ANTI-MARKOVNIKOV ADDITION OF ACIDS TO ALKENES

RELATED APPLICATIONS

This application is a 35 U.S.C. §371 national phase entry of PCT Application PCT/US2013/039707, filed May 6, 2013, and published in English on Nov. 14, 2013, as International Publication No. WO 2013/169651, and which claims the benefit of U.S. Provisional Application No. 61/643,485 filed May 7, 2012, the disclosure of each of which is incorporated herein by reference in its entirety.

STATEMENT OF FEDERAL SUPPORT

This invention was made with Government support under grant no. 1-RO1-GM098340-01 from the National Institutes of Health. The US Government has certain rights to this invention.

FIELD OF THE INVENTION

The present invention concerns methods and catalyst systems useful for carrying out addition reactions, particularly anti-Markovnikov additions of acids to alkenes.

BACKGROUND OF THE INVENTION

Alkenes are one of the most abundant fine chemical feedstocks, readily accessible from both petrochemical and agrochemical sources. Due to their availability, a multitude of methods have evolved for converting alkenes into the fine chemicals that provide modern society with medicines, agrochemicals, materials and plastics (B. Trost and I. Fleming, Comprehensive Organic Synthesis (1991). One of the most important synthetic reactions of alkenes is with acids, comprising a cornerstone of reactivity in organic synthesis. Moreover, this reaction is integral to the catalysis of important processes such as cationic olefin polymerization (G. Odian, in Principles of Polymerization, 372-463 (2004)) and the addition of nucleophiles to alkenes (Trost and Fleming, supra; M. Beller et al., *Angew. Chem. Int. Ed.* 43, 3368 (2004)). The regioselectivity of these addition reactions is dictated by a chemical principle, known as Markovnikov's rule, whereby acids add across nucleophilic carbon double bonds to give a preferred site selectivity (M. B. Smith, J. March, March's Advanced Organic Chemistry (2001)). Generally, the alkene and acid polarities align to give the chemical branching depicted in FIG. 1, precluding the direct formation of the opposite, or anti-Markovnikov, isomeric adducts. This has limited the types of chemical structures that can be directly forged via this fundamental organic transformation.

To reverse Markovnikov regioselection is no trivial task and has been cited as one of the preeminent challenges for catalysis in the new century (J. Haggin, Chem. Eng. News 71, 23 (1993)). After decades of effort, the most viable methods are indirect (e.g. alkene hydroboration and oxidative functionalization) and are designed to circumvent the strong bias against the anti-Markovnikov products. Recent disclosures of transition metalcatalyzed direct anti-Markovnikov addition reactions have made strides to reverse this trend but are limited in scope with respect to both acid and alkene (M. Beller et al., supra; G. Dong et al., *Science* 333, 1609 (2011), M. Utsunomiya et al, *J. Am. Chem. Soc.* 125, 5608 (2003)). The development of a general and straightforward catalytic strategy to access anti-Markovnikov site selectivity has remained to be identified.

SUMMARY OF THE INVENTION

A first aspect of the invention is a method of making an anti-Markovnikov addition product, comprising: reacting an acid with an alkene or alkyne in a dual catalyst reaction system to the exclusion of oxygen to produce said anti-Markovnikov addition product; the dual catalyst reaction system comprising a single electron oxidation catalyst in combination with a hydrogen atom donor catalyst. The anti-Markovnikov addition product is produced regioselectively in a ratio (weight or molar) of at least 5:1 (or in some embodiments at least 10:1, 20:1, 50:1 or 100:1) of anti-Markovnikov addition product as compared to the corresponding Markovnikov addition product.

A second aspect of the invention is a dual catalyst composition for making an anti-Markovnikov addition product by reacting an acid with an alkene, said dual catalyst composition comprising, consisting of or consisting essentially of a single electron oxidation catalyst in combination with a hydrogen atom donor catalyst, and typically a solvent.

The present invention is explained in greater detail in the drawings herein and the specification set forth below. The disclosures of all US Patent references cited herein are to be incorporated herein by reference.

BRIEF DESCRIPTION OF THE DRAWINGS

FIG. 1. Regioselectivity in addition reactions of mineral and organic acids to olefins.

FIG. 2. Cation radicals as potential reactive intermediates in anti-Markovnikov addition reactions of acids to alkenes.

FIG. 3. Proposed Catalytic Cycle for Intramolecular Alkene Anti-Markovnikov Hydroalkoxylation.

FIG. 4. (A) Alkene anti-Markovnikov hydrolactonization catalyzed by 4. (B) Anti-Markkovnikov addition of acetic acid to anethole catalyzed by 4. Alkene oxidation potentials were measured in MeCN with 0.1 M Bu4N+ClO4- and Ag/AgCl as the reference electrode.

DETAILED DESCRIPTION OF THE PREFERRED EMBODIMENTS

1. Definitions

"Addition reaction" as used herein includes both intermolecular addition reactions and intramolecular (e.g., ring-forming) addition reactions.

"Acid" as used herein with reference to reactants in reactions of the present invention may be any suitable acid, typically a Brønsted-Lowry acid, including but not limited to inorganic acids, carboxylic acids, alcohols, amines, thiols, water, malonates, etc.

"Electron withdrawing" group or substituent as used herein describes an atom or group thereof that acts to draw electrons away from another group or substituent. Examples of suitable electron withdrawing substituents include, but are not limited to, halogens (F, Cl, Br, I), nitriles (CN), carboxylic acids (COOH), carbonyls (CO), nitro, aryl (unsubstituted or substituted with electron withdrawing groups), amide (further substituted with alkyl, electron withdrawing groups), sulfonyl (further substituted with alkyl, aryl, electron withdrawing groups), etc.

"Alkyl" as used herein alone or as part of another group, refers to a straight, branched chain, or cyclic, saturated or unsaturated, hydrocarbon containing from 1 or 2 to 10 or 20 carbon atoms, or more. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "akyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cyclo alkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. Alkyl may be saturated or unsaturated and hence the term "alkyl" as used herein is inclusive of alkenyl and alkynyl when the alkyl substituent contains one or more unsaturated bond (for example, one or two double or triple bonds). The alkyl group may optionally contain one or more heteroatoms (e.g., one, two, or three or more heteroatoms independently selected from O, S, and NR', where R' is any suitable substituent such as described immediately above for alkyl substituents), to form a linear heteroalkyl or heterocyclic group as specifically described below.

"Alkenyl" as used herein refers to an alkyl group as described above containing at least one double bond between two carbon atoms therein.

"Alkynyl" as used herein refers to an alkyl group as described above containing at least one triple bond between two carbon atoms therein.

"Alkylene" as used herein refers to an alkyl group as described above, with one terminal hydrogen removed to form a bivalent substituent.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S cyclo alkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical or a —N(ROC(O)R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

2. Acids

Acids used to carry out the invention may be compounds of the Formula H—X, where X is an organic or inorganic group. Suitable examples of inorganic acids that may be used to carry out the present invention include, but are not limited to, HF, HI, HCl, perchloric acid, nitric acid, sulfuric acid, etc. Suitable examples of organic acids include compounds of the formulas: ROH; RSH; RCOOH; R$_2$NH; and ROC(O)CH$_2$C(O)OR; where each R is an independently selected organic substituent, such as alkyl, alkenyl, alkynl, cycloalkyl, cycloalkenyl, cycloalkynyl, aryl, or covalently coupled combinations thereof such as arylalkyl, alkylaryl, etc. Each may be substituted or unsubstituted, and may optionally contain heteroatoms. In embodiments where the reaction is used to polymerize one or more monomers, at least one of the R groups is alkenyl (optionally substituted) as described further below.

3. Alkenes and Alkynes

Any suitable alkene (or olefin) or alkyne can be used to carry out the present invention. In some embodiments the alkenes or alkynes may be of the formulas:

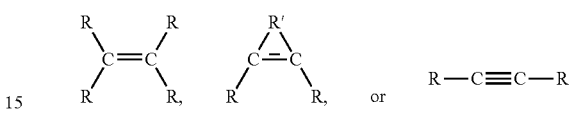

Where each R is independently any suitable substituent such as alkyl, aryl, arylalkyl, alkylaryl, etc., and R' is alkylene (including substituted and unsubstituted embodiments thereof, and optionally heteroatom-containing embodiments thereof, as described above). In some embodiments, such as where the reaction is used to polymerize monomers, the alkene is also an acid. Particular examples of suitable alkenes include but are not limited to those described below.

4. Single Electron Oxidation Catalysts

Any suitable single electron oxidation catalyst can be used to carry out the present invention, including ground state oxidation catalysts and photocatlysts.

Examples of suitable ground state oxidation catalysts include, but are not limited to, ceric ammonium nitrate, ferrocenium tetrafluoroborate, nitrosyl tetrafluoroborate, iron trichloride, iron (III) tris(phenanthroline) tris(hexafluorophosphate), tris(4-bromophenyl)aminium hexafluoroantimonate, etc.

In some embodiments, the single electron oxidation catalyst is a photocatalyst. Such photocatalysts are known and described in, for example, U.S. Pat. No. 4,937,292 and US Patent Application Publication No. 20070215455 (the disclosures of which are incorporated herein by reference in their entirety). In some embodiments, such photocatalysts have a reduction potential of −1.0 V to +0.1 V against a saturated calomel electrode in 100 percent acetonitrile (as determined by cyclic voltammetry) and have the earliest onset of their emission between 350 and 650 nm. (that is, an excited state reduction potential between +0.5 V to +3.6 V vs. SCE in acetonitrile). Example photocatalysts include, but are not limited to, phenazine, eosin, thiobenzophenone, 9,10-dichloroanthracene, 3,4-benzopyrene, perylene, trans-1,3,5-hexatriene, 1-chloroanthracene, 1,5-dichloroanthracene, 1,10-dichloroanthracene, 1,5,10-trichloroanthracene, 1,4,5,8-tetrachloroanthraoene, 9,10-dibromoanthraoene, 9-methylanthracene, 9-nitroanthracene, 1-azaanthracene, 2-azaanthracene, acridine, diphenylbutadiene, 3,4,8,9-dibenzopyrene, 7,12-dimethylbenzanthracene, 1,12-benzoperylene trans-1,2-benzanthracene, 9,10-dicyanoanthracene 1,4-dicyanobenzene and 2,4,6-triphenyloxopyrylium tetrafluoroborate.

In some embodiments, the photocatalysts are carbocyclic or heterocyclic aromatic compounds, for example heterocyclic aromatic compounds containing ring nitrogen heteroatoms.

In some embodiments, the photocatalysts are compounds having an anthracene, azaanthracene or polyaza-anthracene nucleus which is unsubstituted, substituted or polysubstituted at any positions with halogens, except iodine, and/or with one or more lower alkyl or cycloalkyl radicals, and/or with other phenyl substituents.

5. Hydrogen Atom Donor Catalysts

Any suitable hydrogen atom donor catalyst can be used to carry out the present invention. Examples include, but are not limited to compounds such as:

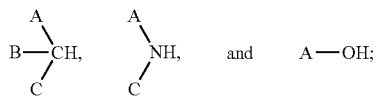

wherein at least one, two, or all three of each A, B, and C is, when present, an independently selected electron withdrawing group. The others of A, B, and C are any suitable substituent, such as either electron neutral groups or mild electron donating groups (e.g., hydrogen, alkyl, and amide group coupled via the nitrogen thereof). The electron neutral or mild electron donating groups are, when present, selected so that the total electrical effect of all groups A, B, and C on the remaining substituent is electron withdrawing.

6. Catalyst Systems and Methods

Reactions of the invention are, in general, carried out in a solvent comprising a polar organic solvent, and optionally including water. Catalyst or reaction systems of the invention comprise the catalysts described above in a solvent, to which the acid and alkene or alkyne may be added to carry out the reaction. Depending on the choice of catalysts, in some embodiments the catalyst systems are free of transition metal catalysts. The catalysts may be provided in an equimolar amount any suitable molar ratio; e.g., from 1:100 or 1:50 to 50:1 or 100:1.

Preferably, the systems are provided and the methods are carried out to the exclusion of oxygen. This may be achieved in accordance with known techniques, such as by filling the gas phase of the reaction vessel or blanketing the liquid phase with an inert, protective or noble gas such as nitrogen, helium or argon. See, e.g., U.S. Pat. Nos. 3,959,307; 5,604,919; and 5,777,146.

The solvent may be protic or aprotic. Examples of suitable solvents include, but are not limited to, ethanol, methanol, acetonitrile, and halogenated solvents such as chloroform, dichloromethane, dichloroethane, etc. Time, temperature and pressure is not critical, but in general the reactions may be carried out at a temperature of −100 or −70° C. up to 70 or 100° C.

Specific types of reactions that can be carried out by the methods of the present invention include, but are not limited to: intramolecular hydroalkoxylation reactions, intramolecular hydrolactonization reactions, intermolecular hydroacetoxylation reactions, and anti-Markovnikov polymerization reactions where the acid and alkene group are contained within the same monomeric unit (e.g., to produce a homopolymer) or are contained on separate monomeric units (e.g., to produce a copolymer).

The present invention is explained in greater detail in the following non-limiting Examples.

Examples

We propose that a new catalytic strategy is required to move toward an all-encompassing solution to the anti-Markovnikov problem. To this end, we considered the reactivity profile of oxidized alkenes, cation radicals (1), as potential key mediators in this process (FIG. 2) (M. Schmittel et al., Angew. Chem. Int. Ed. 36, 2550 (1997)). Transient nucleophilic adducts of substituted styrene cation radicals with various alcohols, amines and anionic species ($N_3^-$, $Cl^-$, $Br^-$, $H_3CCO_2^-$) have been characterized by laser flash photolysis and in all cases, radical 3 (R=Ar), the anti-Markovnikov adduct, was the exclusive intermediate observed (ix). Density functional theory calculations suggest the intermediacy of three-membered cation radical 2 is likely responsible for selective formation of 3 via proton loss and rupture of the more labile C—X bond (x). We speculated that if a single electron oxidation catalyst system could be identified to serve as an effective electron transport to first oxidize the alkene to cation radical 1 and then reduce radical 3 directly or via the intervention of a co-catalyst, a direct catalytic anti-Markovnikov addition could be achieved.

Sporadic reports of single electron oxidant-promoted anti-Markovnikov transformations support this proposal (R. Neuteufel and D. Arnold, J. Am. Chem. Soc. 95, 4080 (1973)). Yamashita and Gassman have disclosed anti-Markovnikov alkene hydroamination (H—X=H—$NR_2$) and hydrolactonization (H—X=H—$O_2CR$) reactions, respectively, making use of cyanoarenes (i.e. 1-cyanonaphthalene and 1,4-dicyanobenzene) as single electron photooxidants (T. Yamashita et al., Tetrahedron 50, 9275 (1994); P. Gassman and K. Bottorff, J. Am. Chem. Soc. 109, 7547 (1987)). Though noteworthy, these reports required either superstoichiometric quantities of the oxidant, are low yielding, or hampered by significant amounts of byproduct formation (including oxidant incorporation into the substrate). Additional reports of anti-Markovnikov alcohol additions to alkenes rely specifically on 1,1-diarylethylenes as reactants (likely via exciplex formation) and therefore do not offer significant latitude with regard to olefin structure (K. Mizuno, et al., Chem. Lett. 1095 (1989), K. Mizuno et al., Angew. Chem. Int. Ed. 33, 2113 (1994), S. Asaoka et al., J. Am. Chem. Soc. 121, 8486 (1999)). Though a valuable starting point for investigation, a synthetically useful and general catalytic anti-Markovnikov system awaits discovery. Herein we report the development of a general catalyst system that effects anti-Markovnikov additions of a range of oxy-acids (H—OR) to an array of electronically and structurally diverse alkenes with complete regioselectivity via the intermediacy of cation radicals.

As a starting point, we elected to pursue an intramolecular anti-Markovnikov hydroalkoxylation of alkenols, a largely elusive transformation in organic synthesis. This reaction class would give direct access to cyclic ether structures found in many biologically active compounds as well as provide valuable building blocks to organic synthesis. Based on prior mechanistic hypotheses, we perceived that the critical step preventing catalyst turnover was the single electron reduction of radical intermediate 3 (FIG. 2). In order to remedy this issue, we recognized good candidates for a single electron oxidation catalyst must exhibit the following characteristics:

i) nearly complete redox reversibility ii) a high reduction potential capable of oxidizing alkenes in the range of +1.0 V to +2.0 V iii) is positively charged to minimize unproductive back electron transfer to 1 via minimization of coulombic attraction and iv) the subsequent reduced form could itself, be a potent reductant. Reports of commercially available 9-mesityl-10-methylacridinium perchlorate (4) drew our attention as a photooxidant for this application (S. Fukuzumi et al., *J. Am. Chem. Soc.* 126, 1600 (2004)). Given the acridinium moiety's strong absorption band in the visible region ($\gamma$=430 nm), high excited state oxidation power ($E_{1/2}^{red*}$=+2.06 V vs. SCE) (K. Ohkubo et al., *Chem. Commun.* 46, 601 (2010)), and utility in a number of reported transformations (H. Kotani et al., *J. Am. Chem. Soc.* 126, 15999 (2004)), K. Ohkubo et al., *Org. Lett.* 7, 4265 (2005)), we predicted that cation radicals could be conveniently generated from an electronically diverse range of alkenes. Additionally, the reduced form of the acridinium catalyst (5) is a strong reductant ($E_{1/2}^{ox}$=−0.57 V vs. SCE) that we presumed might be capable of back electron transfer to radical intermediate 3, a key, but ill-defined step in the overall catalytic process.

To test this hypothesis, we subjected alkenol 6 to 5 mol % of catalyst 4 in degassed 1,2-dichloroethane (DCE) under irradiation with 450 nm LEDs. As anticipated, we observed the anti-Markovnikov adduct, tetrahydrofuran 7, albeit in low yields (36% yield, Table 1, Entry 1). Though even trace amounts of the Markovnikov adduct were not observed and conversion of the starting alkenol was relatively good (86%), yields were severely hampered by extensive byproduct formation, most of which could not be identified and most likely arose from competing radical processes. A control experiment in which alkenol 6 was submitted to 30 mol % of $HOSO_2CF_3$ afforded the anticipated tetrahydropyran Markovnikov adduct in 55% yield.

We speculated that the key to higher levels of reaction efficiency lay in the reduction of radical 3 to its respective anion. To avoid this potentially endergonic reduction pathway, we proposed an intervening radical exchange via hydrogen atom abstraction facilitated by an H-atom redox catalyst (8) to produce a radical capable of acting as a single electron oxidant (FIG. 3). In order to achieve this goal, we sought organic molecules that could act as hydrogen atom donors, whose subsequent radicals (9) could serve as an oxidant for the reduced acridinium catalyst (5).

Potential hydrogen atom donors were selected on the basis of their respective homolytic bond energies. To ensure exothermic hydrogen atom transfer, we limited our survey to H-atom redox catalysts possessing X—H bonds of <90 kcal/mol (Table 1, Entries 2-4) (xxi). Though 0.5 equivalents of either N-hydroxyphthalimide (BDE=87 kcal/mol, Entry 2) or 9-phenylfluorene (BDE=74 kcal/mol) gave modest increases in reaction efficiency, we were pleased to find that 2-phenylmalononitrile (8), with a bond dissociation energy of 77 kcal/mol (T. Yamashita et al., *Tetrahedron* 50, 9275 (1994)), was uniquely suited to this application and gave the 5-exo adduct in 73% yield (Entry 4). The majority of the remaining mass balance was attributed to oxidative cleavage of the olefin, presumably via interception of radical intermediates with adventitious oxygen. Further control experiments demonstrate that both the acridinium photocatalyst and light are absolutely necessary for reactivity (Entries 6-7). The utility of the acridinium catalyst as the single electron photooxidant is underscored when compared directly with the frequently employed $Ru(bpy)_3^{2+}$, which failed to give any of the desired adduct (Entry 5). This result can be understood by comparing the oxidation potential of the alkenol ($E_{ox}$=+1.95 V vs. Ag/AgCl in MeCN) to the excited state reduction potential of $Ru(bpy)_3^{3+}$ ($E_{1/2}^{red}$=+1.33 V vs. SCE), indicating that electron transfer is endergonic. We believe this result demonstrates the utility of acridinium catalysts as a visible light single electron photooxidants and should allow for greater latitude in potential substrates with alkenes possessing oxidation potential ranging up to +2.0 V (The $BF_4^-$ salt of catalyst 4 can be employed without significant variation in yields). Furthermore, there are few, if any ground state single electron chemical oxidants, to our knowledge, that possess the oxidizing capabilities found in the acridinium catalyst (N. Connelly and W. Geiger, *Chem. Rev.* 96, 877 (1996)).

We postulate that the utility of 2-phenylmalononitrile arises from the unique oxidizing properties of the conjugate radical of 2-phenylmalononitrile, as it is more prone to reduction than oxidation (We estimate the reduction potential of the conjugate radical of PhCH(CN)2 to be +0.27 V vs. SCE based on the reported oxidation potential of PhC(CN)2-.) (P. Maslak et al., *J. Am. Chem. Soc.* 113, 2304 (1991)), (As a result, the reduction event that had previously hindered consistency across a broad scope of substrates can be overcome). Application of optimized conditions across a broad scope of olefin types demonstrates that intramolecular hydroalkoxylation using this method is possible across a wide range of olefin electronics, from electron rich to electron neutral, up to the point where the oxidation potential of the olefins dramatically exceed the excited state reduction potential of the acridinium catalyst.

Having identified a viable catalyst system, we set out to investigate the scope of the intramolecular anti-Markovnikov hydroalkoxylation of alkenols (Table 2). A number of electronically diverse styrenes (Entries 1-3) ranging from electron rich (4-(MeO)$C_6H_4$, Entry 2; 83% yield) to electron deficient (4-$ClC_6H_4$, Entry 3; 61%) provided good yields of the 5-exo adducts. Additionally, Thorpe-Ingold assistance is not required in the backbone of the molecule, as the substrate in Entry 4 gave nearly identical levels of reaction efficiency (84% yield) as that in Entry 2 (83% yield) that lacked the geminal dimethyl substituent. Moreover, the mild reaction conditions are highlighted in Entry 8, where a silyl-protected alcohol remains unperturbed following the cyclization. A gram scale reaction of the alkenol in Entry 6 produced the expected tetrahydrofuran product in 77% isolated yield, further demonstrating the utility of this process.

TABLE 1

Reaction optimization and control experiments.*

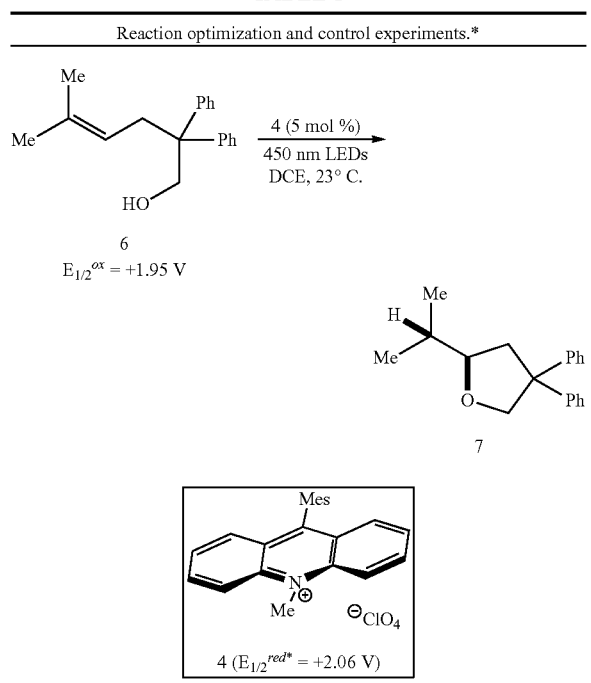

| Entry | Conditions | Conversion† | Yield† |
|---|---|---|---|
| 1 | Standard Conditions | 83% | 36% |
| 2 | With 0.5 equiv N-hydroxyphthalimide | 48% | 41% |
| 3 | With 0.5 equiv 9-phenylfluorene | 78% | 51% |
| 4 | With 0.5 equiv PhCH(CN)$_2$ | 89% | 73% |
| 5 | Ru(bpy)$_3$(PF$_6$)$_2$ Photooxidant‡,§ | <5% | <5% |
| 6 | No Photooxidant‡ | <5% | <5% |
| 7 | No Light‡ | <5% | <5% |
| 8 | 1,4-Dicyanobenzene Photooxidant | 28% | 7% |

*Reactions run at 0.5M in substrate in degassed DCE with irradiation by a 15 W 450 nm LED flood lamp under an atmosphere of nitrogen.
†Determined by $^1$H NMR analysis of the crude reaction mixture.
‡With 0.5 equiv of PhCH(CN)$_2$.
§With 1.0 equiv of methyl viologen. Irradiated with 10 × 8 W T5 fluorescent bulbs with spectral output >290 nm.

In addition to the formal 5-exo cyclization mode (Entries 1-8), 6-exo (Entry 11) and 7-exo (Entry 12) annulations were possible. Perhaps most intriguing was the tetrahydropyran products obtained in Entries 9 and 10 from formal 6-endo cyclization modes, which are quite challenging to effect in traditional polar reactions given the poor orbital alignment necessary for cyclization (J. E. Baldwin *J. Chem. Soc. Chem. Commun.* 734 (1976)).

Finally, as a testament to the generality of this catalysis mode, we have results concerning additional H—X sources in anti-Markovnikov addition reactions to alkenes (FIG. 4). Treatment of alkenoic acid 10 to the standard conditions in the presence of a mild base (2,6-lutidine) resulted in clean anti-Markovnikov hydrolactonization with complete regioselectivity in 72% isolated yield (FIG. 4A). This system enables an important disconnection in organic synthesis that is likely to find utility in chemical synthesis. Perhaps most importantly, acetic acid itself can engage in an intermolecular hydroacetoxylation with anethole (12) to afford the β-acetoxy addition product 13 exclusively in 73% isolated yield, albeit with increased quantities (2.5 equiv) of PhCH(CN)$_2$ (FIG. 4B).

These results in conjunction with the intramolecular alkene hydroalkoxylation reaction, form a basis of reactivity that demonstrates the utility of this catalysis concept for a general approach to direct anti-Markovnikov addition of acids to alkenes. Moreover, this work provides a series of valuable site selective synthetic transformations likely to find broad application in chemical synthesis The foregoing is illustrative of the present invention, and is not to be construed as limiting thereof. The invention is defined by the following claims, with equivalents of the claims to be included therein.

TABLE 2

Scope of the Intramolecular Alkene Anti-Markovnikov Hydroalkoxylation.

| Entry | Alkenol | Product |
|---|---|---|
| 1 | Ph-alkenol, Me, Me, HO<br>$E_{1/2}^{ox}$ = +1.62 V | Ph product, Me, Me<br>63% yield |
| 2 | Ar-alkenol, Me, Me, HO<br>Ar = 4-(MeO)C$_6$H$_4$<br>$E_{1/2}^{ox}$ = +1.26 V | Ar product, Me, Me<br>80% yield |
| 3 | Ar-alkenol, Me, Me, HO<br>Ar = 4-(Cl)C$_6$H$_4$<br>$E_{1/2}^{ox}$ = +1.69 V | Ar product, Me, Me<br>60% yield |
| 4 | Ar-alkenol, HO<br>Ar = 4-(MeO)C$_6$H$_4$<br>$E_{1/2}^{ox}$ = +1.41 V | Ar product<br>82% yield |
| 5 | Me, Me, Ph, Ph, HO<br>$E_{1/2}^{ox}$ = +1.95 V | Me, Ph, Ph product<br>77% yield |

TABLE 2-continued

Scope of the Intramolecular Alkene Anti-Markovnikov Hydroalkoxylation.

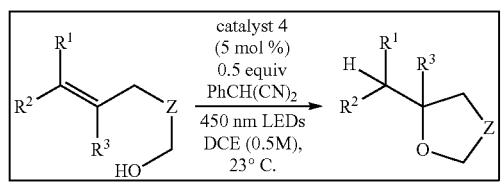

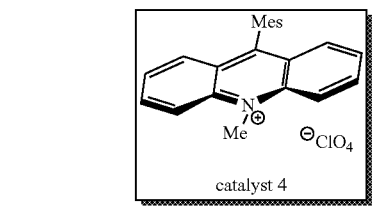

| Entry | Alkenol | Product |
|---|---|---|
| 6* | Me, Me substituted alkenol with Ph, Ph, Me, HO groups; $E_{1/2}^{ox} = +2.10$ V | tetrahydrofuran product with Me, Ph, Ph, Me substituents; 41% yield, 5:1 d.r.† |
| 7* | Me substituted alkenol with TBSO, Ph, Ph, HO groups; $E_{1/2}^{ox} = +1.98$ V, >5:1 E:Z | TBSO-substituted tetrahydrofuran product with Me, Ph, Ph; 41% yield, 1.1:1 d.r.† |
| 8 | Ar-substituted alkenol with i-Pr, HO groups; Ar = 4-(MeO)C$_6$H$_4$; $E_{1/2}^{ox} = +1.30$ V | Ar-substituted tetrahydrofuran with i-Pr; 77% yield, 1.8:1 d.r.† |
| 9 | Ph, Me, Me substituted alkenol with HO group; $E_{1/2}^{ox} = +2.05$ V | Ph, Me, Me-substituted tetrahydropyran; 77% yield |
| 10* | Me, Me substituted alkenol with Ph, HO groups; $E_{1/2}^{ox} = +1.88$ V | Me, Me, Ph-substituted tetrahydropyran; 68% yield, 2.5:1 d.r.† |

TABLE 2-continued

Scope of the Intramolecular Alkene Anti-Markovnikov Hydroalkoxylation.

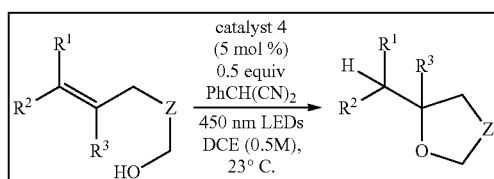

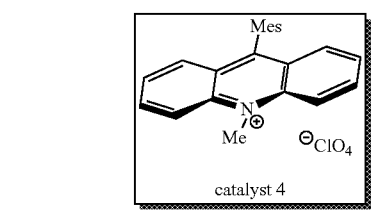

| Entry | Alkenol | Product |
|---|---|---|
| 11* | Me, Me substituted alkenol with Me, HO groups; $E_{1/2}^{ox} = +1.92$ V | Me, Me-substituted oxepane with Me; 46% yield, 1.2:1 d.r.† |

Yields of cyclic ether products averaged from two reactions after 36-144 h. All alkenol oxidation potentials were measured in MeCN with 0.1M Bu$_4$N$^+$ClO$_4^-$ and Ag/AgCl as the reference electrode.
*With 2.0 equiv of PhCH(CN)$_2$.
†Determined by $^1$H NMR analysis of the crude reaction mixture.

That which is claimed is:

1. A method of making an anti-Markovnikov addition product, comprising:

reacting an aliphatic organic acid with an alkene in a dual catalyst reaction system to the exclusion of oxygen to produce said anti-Markovnikov addition product;

said dual catalyst reaction system comprising a single electron oxidation catalyst in combination with a hydrogen atom donor catalyst, wherein said single electron oxidation catalyst has the structure:

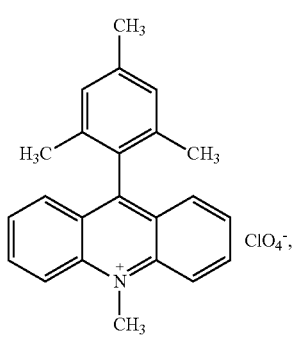

and wherein said hydrogen atom donor catalyst has the structure:

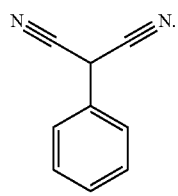 [SMILES: N#CC(C#N)c1ccccc1]

5

2. The method of claim 1, wherein said reacting is an intramolecular hydroalkoxylation reaction.

3. The method of claim 1, wherein said reacting is an intramolecular hydrolactonization reaction.

4. The method of claim 1, wherein said reacting is an intermolecular hydroacetoxylation reaction.

5. The method of claim 1, wherein said reacting is an anti-Markovnikov polymerization reaction where the acid and alkene group are contained within the same monomeric unit or are contained on separate monomeric units.

* * * * *